United States Patent [19]

Sharpe

[11] 4,014,882
[45] Mar. 29, 1977

[54] TRIFLUOROMETHYL SUBSTITUTED PYRIMIDINE DERIVATIVES USEFUL AS INSECTICIDES

[75] Inventor: Stuart Peter Sharpe, Yateley, England

[73] Assignee: Imperial Chemical Industries Limited, London, England

[22] Filed: Jan. 5, 1976

[21] Appl. No.: 646,832

Related U.S. Application Data

[62] Division of Ser. No. 456,383, March 29, 1974.

[30] Foreign Application Priority Data

May 25, 1973 United Kingdom ............ 25207/73

[52] U.S. Cl. ................ 260/256.5 R; 260/256.4 E; 260/256.4 C; 424/251; 71/87
[51] Int. Cl.² ............. C07D 239/30; C07D 239/46
[58] Field of Search ............. 260/256.4 E, 256.5 R

[56] References Cited
UNITED STATES PATENTS 3,287,453 11/1966 McHattie .................... 260/256.4 E
3,657,247 4/1972 Freeman et al. ............ 260/256.4 E
3,928,353 12/1975 Milzner et al. ............. 260/256.4 E Primary Examiner—Donald G. Daus
Assistant Examiner—J. H. Turnipseed
Attorney, Agent, or Firm—Cushman, Darby & Cushman

[57] ABSTRACT

Pesticidally active compounds of the formula:

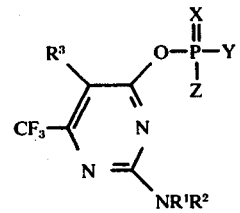

wherein X is oxygen or sulphur; Y and Z are alkoxy containing from one to four carbon atoms; $R^1$ and $R^2$ are alkyl containing from one to four carbon atoms; and $R^3$ is hydrogen or halogen.

8 Claims, No Drawings

TRIFLUOROMETHYL SUBSTITUTED PYRIMIDINE DERIVATIVES USEFUL AS INSECTICIDES

This is a division of application Ser. No. 456,382, filed Mar. 29, 1974, now abandoned.

This invention relates to novel organophosphorus compounds, processes for their preparation, compositions comprising them and methods of combating pests using them.

Accordingly the present invention provides compounds of formula:

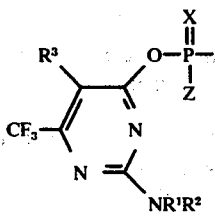

wherein X is oxygen or sulphur; Y and Z are alkoxy containing from one to four carbon atoms; $R^1$ and $R^2$ are alkyl containing from one to four carbon atoms; and $R^3$ is hydrogen or halogen.

In a preferred aspect the invention provides compounds of the above formula wherein X is oxygen or sulphur; Y and Z are both methoxy or ethoxy; and $R^1$ and $R^2$ are both methyl or ethyl; and $R^3$ is hydrogen or chlorine.

Specific examples of compounds according to the invention include those given in Table 1 below wherein the values of $R^1$, $R^2$, $R^3$, X, Y and Z are set out.

TABLE 1

| Compound No. | $R^1$ | $R^2$ | $R^3$ | X | Y | Z |
|---|---|---|---|---|---|---|
| 1 | $CH_3$ | $CH_3$ | H | S | $OCH_3$ | $OCH_3$ |
| 2 | $CH_3$ | $CH_3$ | H | S | $OC_2H_5$ | $OC_2H_5$ |
| 3 | $CH_3$ | $CH_3$ | H | O | $OC_2H_5$ | $OC_2H_5$ |
| 4 | $C_2H_5$ | $C_2H_5$ | H | S | $OC_2H_5$ | $OC_2H_5$ |
| 5 | $C_2H_5$ | $C_2H_5$ | H | S | $OCH_3$ | $OCH_3$ |
| 6 | $CH_3$ | $CH_3$ | Cl | S | $OC_2H_5$ | $OC_2H_5$ |

The invention compounds may be prepared by the process of treating a compound of formula:

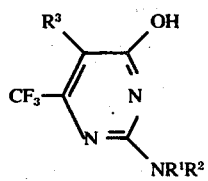

or an alkali metal salt thereof, with a compound of formula:

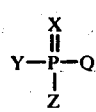

wherein Q is a halogen atom, preferably a chlorine or bromine atom, and $R^1$, $R^2$, $R^3$, X, Y and Z have any of the meanings given hereinbefore.

The above preparation may be carried out in a non-reacting diluent or solvent and in the presence of a base.

The invention compounds may be used to combat pests on their own, but we more conveniently used in the form of a composition comprising the invention compound and also comprising a diluent or carrier.

In a further aspect therefore the present invention also provides pesticidal compositions comprising as an active ingredient a compound of formula:

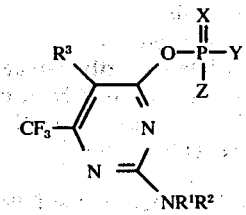

wherein X, Y, Z, $R^1$, $R^2$ and $R^3$ have any of the meanings given hereinbefore, in association with a diluent or carrier.

In a preferred aspect the invention provides pesticidal compositions comprising as an active ingredient any of the compounds set out in Table I herein, in association with a diluent or carrier.

The compositions may be in the form of granular powders wherein the active ingredient is absorbed on a porous granular material, for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents. These compositions are prepared by dissolving the active ingredient in a suitable solvent, for example, a ketonic solvent such as diacetone alcohol, and adding the mixture so obtained to water which may contain one or more known wetting, dispersing or emulsifying agents.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water in order to form aqueous preparations which remain homogeneous for a sufficient time to enable them to be applied by conventional spray equipment. The concentrates may contain 10–85% by weight of the active ingredient or ingredients. When diluted to form aqueous preparations, such preparations may contain varying amounts of the active ingredient depending upon the purpose for which they are to be used.

For agricultural or horticultural purposes, an aqueous preparation containing between 0.0001% and 0.1% by weight of the active ingredient or ingredients may be used.

The compositions of the present invention, may, if desired, also comprise in addition to a compound of the present invention, at least one other biologically-active ingredient, for example an insecticide, or a fungicide.

In use the compositions are applied to the pests, to the locus of the pests, to the habitat of the pests, or to growing plants liable to infestation by the pests, by any of the known means of applying pesticidal compositions, for example by dusting or spraying.

The compounds of the invention and compositions comprising them are very toxic to wide varieties of insect and other invertebrate pests, including, for example, the following:

*Tetranychus telarius* (red spider mites)
*Aphis fabae*, (aphids)
*Megoura viceae* (aphids)
*Aedes aegypti* (mosquitos)
*Musca domestica* (houseflies)
*Pieris brassicae* (white butterfly, larvae)
*Plutella maculipennis* (diamond back moth, larvae)
*Phaedon cochleariae* (mustard beetle)
*Calandra granaria* (grain beetle)

The invention is illustrated by the following examples.

EXAMPLE 1

5 Parts by weight of Compound No. 1 of Table 1 were thoroughly mixed in a suitable mixer with 95 parts by weight of talc. There was thus obtained a dusting powder.

EXAMPLE 2

10 Parts by weight of Compound No. 2 of Table 1 10 parts of an ethylene oxide-octylphenol condensate ("Lissapol" NX; "Lissapol" is a Trade Mark) and 80 parts by weight of diacetone alcohol were thoroughly mixed. There was thus obtained a concentrate which, in mixing with water, gave an aqueous dispersion suitable for application as a spray in the control of insect pests.

EXAMPLE 3

A granular composition was prepared by dissolving the active ingredient in a solvent, spraying the solution obtained on to the granules of pumice and allowing the solvent to evaporate.

|  | % wt. |
|---|---|
| Compound No. 3 of Table 1 | 5 |
| Pumice Granules | 95 |
|  | 100% |

EXAMPLE 4

An aqueous dispersion formulation was prepared by mixing and grinding the ingredients recited below in the proportions stated.

|  | % wt. |
|---|---|
| Compound No. 4 of Table 4 | 40 |
| Calcium lignosulphonate | 10 |
| Water | 50 |
|  | 100% |

EXAMPLE 5

The activity of a number of the compounds was tested against a variety of insect and other invertebrate pests. The compounds were used in the form of a liquid preparation containing 0.1% by weight of the compound except in the test with *Aedes aegypti* where the preparations contained 0.01% by weight of the compound. The preparations were made by dissolving each of the compounds in a mixture of solvents consisting of 4 parts by volume of acetone and 1 part by volume of diacetone alcohol. The solutions were then diluted with water containing 0.01% by weight of a wetting agent sold under the trade name "Lissapol" NX until the liquid preparations contained the required concentration of the compound "Lissapol" is a Trade Mark.

The test procedure adopted with regard to each pests was basically the same and comprised supporting a number of the pests on a medium which was usually a host plant or a foodstuff on which the pests feed, and treating either or both the pests and the medium with the preparations.

The mortality of the pests was then assessed at periods usually varying from 1 to 3 days after the treatment.

The results of the tests are given below in Table 2. In this table the first column indicates the name of the pest species. Each of the subsequent columns indicates the host plant or medium on which it was supported, the number of days which were allowed to elapse after the treatment before assessing the mortality of the pests, and the results obtained for each of the compounds, numbered as in Table I above. The assessment is expressed in integers which range from 0–3.

0 represents less than 30% kill
1 represents 30–49% kill
2 represents 50–90% kill
3 represents over 90% kill A dash (—) in Table 2 indicates that no test was carried out.

TABLE 2

| Pest Species | Support Medium | No. Days | Compound No. 1 | 2 | 3 | 4 | 5 | 6 |
|---|---|---|---|---|---|---|---|---|
| Tetranychus telarius (red spider mites, adults) | French Bean | 3 | 3 | 3 | 3 | 3 | 0 | 2 |
| Aphis fabae (green aphids) | Broad Bean | 2 | 3 | 3 | 3 | 3 | 3 | 2 |
| Megoura viceae (black aphids) | Broad Bean | 2 | 0 | 3 | 3 | 2 | 0 | 0 |
| Aedes aegypti (mosquito adults) | Plywood | 1 | 3 | 3 | 2 | 3 | 3 | 3 |
| Musca domestica (houseflies-contact test) | Milk/Sugar | 2 | 3 | 3 | 3 | 3 | 3 | 3 |
| Musca domestica (houseflies-residual test) | Plywood | 2 | 3 | 3 | 3 | 3 | 3 | 3 |
| Pieris brassicae (cabbage white caterpillars contact test) | Cabbage | 2 | 3 | 3 | 3 | 3 | 3 | 3 |
| Plutella maculipennis (diamond back moth larvae-residual test) | Mustard | 2 | 0 | 0 | 3 | 3 | 3 | 0 |
| Phaedon cochleariae (mustard beetles-residual test) | Mustard | 2 | 3 | 3 | 3 | 3 | 3 | 3 |
| Calandra granaria (grain beetles) | Grain | 2 | 3 | 3 | 3 | 3 | 3 | 0 |
| Aedes aegypti (mosquito larvae) | Water | 1 | 0 | 3 | 3 | 0 | 3 | 3 |

In the foregoing Table "contact test" indicates that both the pests and the medium were treated, and "residual test" indicates that the medium was treated before infestation with the pests,

EXAMPLE 6

This example illustrates the preparation of O,O-diethyl 2-dimethylamino-4-trifluoromethylpyrimidin-6-yl phosphate (Compound No. 3, Table 1) having the formula:

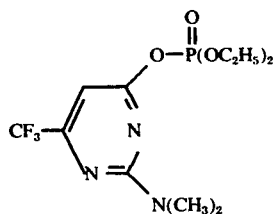

A mixture of 2-dimethylamino-4-trifluoromethyl-6-hydroxypyrimidine (3.1), anhydrous potassium carbonate (2.8 g), and dry ethyl acetate (50 ml) was refluxed together for 1 hour and then cooled to about 40° C. Diethylphosphorochloridate (2.54 g) was then added dropwise to the stirred mixture and when the addition was complete the mixture was refluxed for 16 hours, after which it was allowed to cool to the ambient temperature. After filtration to remove the solids present, the filtrate was washed with water (2 × 50 ml), 10% w/v aqueous sodium hydroxide solution (1 × 55 ml), and finally with water until the washings were neutral. The ethyl acetate solution was dried over anhydrous magnesium sulphate, and after filtering, the the solvent was evaporated under reduced pressure to yield a residual pale yellow oil, which on cooling and scratching yielded crystalline O,O-diethyl 2-dimethylamino-4-trifluoromethylpyrimidin-6-yl phosphate, melting point 22°–24° C.

EXAMPLE 7

By a process similar to that illustrated in Example 6 each of the compounds numbered 1,2,4,5 and 6 in Table 1 was prepared from the appropriate starting materials, thus:

O,O-dimethyl 2-dimethylamino-4-trifluoromethyl-pyrimidin-6-yl phosphorothionate (Compound No. 1, Table 1) was prepared from 2-dimethylamino-4-trifluoromethyl-6-hydroxypyrimidine and diethylphosphorochloridothionate, and had a refractive index of $N_D^{25}$ 1.4940

O,O-diethyl 2-dimethylamino-4-trifluoromethyl-pyrimidin-6-yl phosphorothionate (Compound No. 2, Table 1) was prepared from 2-dimethylamino-4-trifluoromethyl-6-hydroxypyrimidine and diethylphosphorochloridothionate, and had a refractive index of $N_D^{20}$ 1.4860;

O,O-Diethyl 2-diethylamino-4-trifluoromethyl-pyrimidin-6-yl phosphorothionate (Compound No. 4, Table 1) was prepared from 2-diethylamino-4-trifluoromethyl-6-hydroxyprimidine and diethyphosphorochloridothionate, and had a melting point 25°–27° C.

O,O-Dimethyl 2-diethylamino-4-trifluoromethyl-pyrimidin-6-yl phosphorothionate (Compound No, 5 Table 1) was prepared from diethylamino-4-trifluoromethyl-6-hydroxyprimidine and dimethylphosphorochloridothionate, and had a melting point of 27°–29° C; and O,O-Diethyl 2-dimethylamino-5-chloro-4-trifluoromethyl-pyrimidin-6-yl phosphorothionate was prepared from 2-dimethylamino-5-chloro-4-trifluoromethyl-6-hydroxypyrimidine and diethylphosphorochloridothionate, and has a melting point of 30°–32° C.

I claim:

1. A compound of formula:

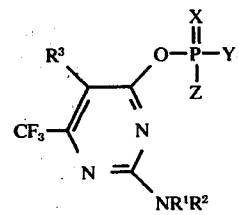

wherein X is oxygen or sulphur; Y and Z are alkoxy having from one to four carbon atoms; $R^1$ and $R^2$ are alkyl having from one to four carbon atoms; and $R^3$ is hydrogen or halogen.

2. A compound according to claim 1 wherein X is oxygen or sulphur; Y and Z are both methoxy or ethoxy; $R^1$ and $R^2$ are both methyl or ethyl; and $R^3$ is hydrogen or chlorine.

3. A compound according to claim 1 which is:
O,O-Dimethyl O-2-dimethylamino-4-trifluoromethylpyrimidin-6-yl phosphorothionate.

4. A compound according to claim 1 which is O,O-diethyl O-2-dimethylamino-4-trifluoromethyl-pyrimidin-6-yl phosphorothionate.

5. A compound according to claim 1 which is O,O-diethyl O-2-dimethylamino-trifluoromethyl-pyrimidin-6-yl phosphate.

6. A compound according to claim 1 which is O,O-diethyl O-2-diethylamine-4-trifluoromethyl-pyrimidin-6-yl phosphorothionate.

7. A compound according to claim 1 which is O-O-dimethyl O-2-diethylamino-4-trifluoromethyl-pyrimidin-6-yl phosphorothionate.

8. A compound according to claim 1 which is O,O-diethyl O-2-dimethylamino-5-chloro-4-trifluoromethylpyrimidin-6-yl phosphorothionate.

* * * * *